US010406102B2

(12) United States Patent
Libin et al.

(10) Patent No.: US 10,406,102 B2
(45) Date of Patent: Sep. 10, 2019

(54) HYPERCOMPRESSED PHARMACEUTICAL FORMULATIONS

(71) Applicant: Sustained Nano Systems LLC, Westhampton Beach, NY (US)

(72) Inventors: Barry M. Libin, Westhampton Beach, NY (US); Jeffrey M. Liebmann, Great Neck, NY (US); Weiliam Chen, Mt. Sinai, NY (US)

(73) Assignee: SUSTAINED NANO SYSTEMS LLC, Westhampton Beach, NY (US)

( * ) Notice: Subject to any disclaimer, the term of this patent is extended or adjusted under 35 U.S.C. 154(b) by 0 days.

(21) Appl. No.: 16/032,025

(22) Filed: Jul. 10, 2018

(65) Prior Publication Data

US 2019/0015336 A1 Jan. 17, 2019

Related U.S. Application Data

(60) Provisional application No. 62/531,264, filed on Jul. 11, 2017.

(51) Int. Cl.
A61K 9/16 (2006.01)
A61K 39/395 (2006.01)
A61K 9/00 (2006.01)
A61K 9/50 (2006.01)
C07K 16/22 (2006.01)

(52) U.S. Cl.
CPC .......... A61K 9/1647 (2013.01); A61K 9/0019 (2013.01); A61K 9/0053 (2013.01); A61K 9/5031 (2013.01); A61K 9/5089 (2013.01); A61K 39/39591 (2013.01); A61K 39/3955 (2013.01); C07K 16/22 (2013.01); C07K 2317/24 (2013.01); C07K 2317/76 (2013.01)

(58) Field of Classification Search
None
See application file for complete search history.

(56) References Cited

U.S. PATENT DOCUMENTS

| 5,134,122 A | 7/1992 | Orsolini | |
|---|---|---|---|
| 2002/0136776 A1 | 9/2002 | Fang et al. | |
| 2008/0292680 A1 | 11/2008 | Libin | |
| 2008/0305147 A1 | 12/2008 | Macdonald et al. | |
| 2009/0148498 A1* | 6/2009 | Libin | A61K 9/0051 424/427 |
| 2009/0270308 A1 | 10/2009 | Libin et al. | |
| 2009/0281070 A1 | 11/2009 | Kaltsatos | |
| 2012/0277690 A1 | 11/2012 | Schachter et al. | |
| 2013/0189369 A1* | 7/2013 | Marsh | A61K 47/34 424/497 |
| 2017/0095569 A1 | 4/2017 | Alargova et al. | |

FOREIGN PATENT DOCUMENTS

| CA | 2353809 A1 | 6/2000 |
|---|---|---|
| CA | 2485932 A1 | 12/2002 |
| JP | 58-099411 A | 6/1983 |
| JP | 03-066625 A | 3/1991 |
| JP | 2001-506144 A | 5/2001 |
| JP | 2005-8598 A | 1/2005 |
| JP | 2008-851144 A | 4/2008 |
| WO | 98/24504 | 6/1998 |
| WO | 00/33820 | 6/2000 |
| WO | 2006/017852 A2 | 2/2006 |
| WO | 2006/072685 A1 | 7/2006 |
| WO | 2010/123563 A2 | 10/2010 |

OTHER PUBLICATIONS

Gentile et al.; "An Overview of Poly(lactic-co-glycolic) Acid (PLGA)-Based Biomaterials for Bone Tissue Engineering"; Int. J. Mol. Sci. (2014), 15, pp. 3640-3659. Published Feb. 28, 2014.*
Notification of Transmittal of the International Search Report and the Written Opinion of the International Searching Authority for PCT/US2018/041530 dated Oct. 1, 2018.
Handbook of Polymer Applications in Medicine and Medical Devices, Kayon Modjarrad et al. Ed. pp. 38-39, Elsevier (2013).
The effect of lauryl capping group on protein release and degradation of poly(D,L-lactic-co-gylcollic acid) particles, Journal of Controlled Release, 172 (2013) pp. 436-443.
Preparation of Biodegradable Microspheres and Matrix Devices Containing Naltrexone, Rassoul Dinarvand et al. AAPS PharmSciTech 2003,4(3) Article 34(http:www.pharrnscitech.org).
English Abstract for JP2001-506144A.
English Abstract for JP 2008-511544.
English Abstract for JP 2005-008598.
English Abstract for JP 58-099411.
English Abstract for JP 03-066625.

* cited by examiner

Primary Examiner — Jeffrey T. Palenik
(74) Attorney, Agent, or Firm — Hedman & Costigan, P.C.; James V. Costigan; Kathleen A. Costigan

(57) ABSTRACT

A pharmaceutical dosage form which comprises a lactide, glycolide or lactide-glycolide polymer, a block polymer of polyglycolide, trimethylene carbonate, poly-caprolactone, and polyethylene oxide that is combined with a peptide or protein therapeutic agent in the form of microparticles which are compressed using a pressure of 50,000 to 350,000 psi.

8 Claims, 1 Drawing Sheet

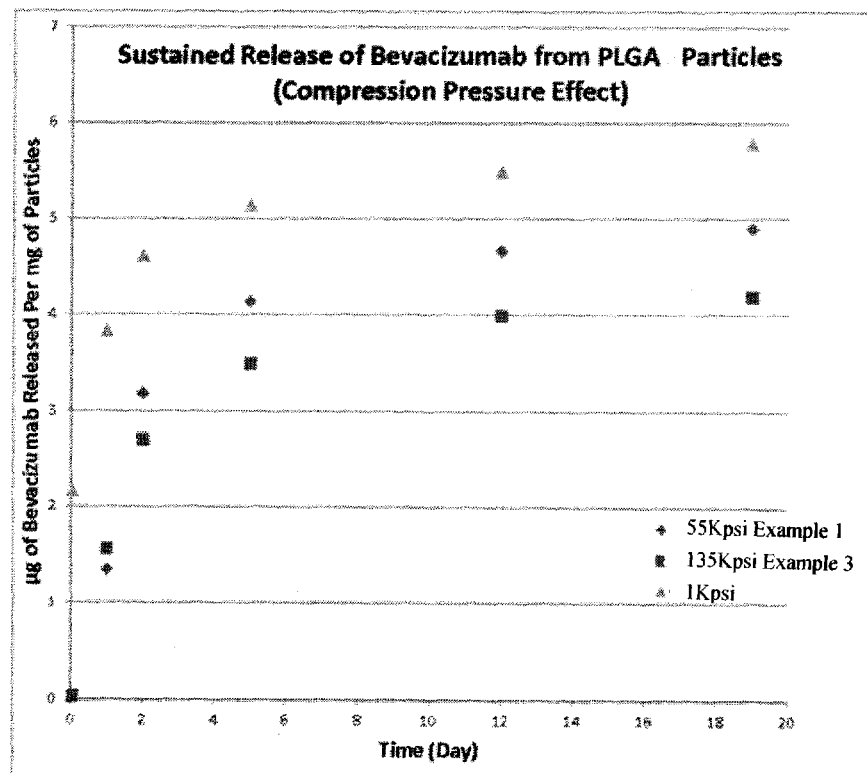

HYPERCOMPRESSED PHARMACEUTICAL FORMULATIONS

This application claims the priority of Provisional Application Ser. No. 62/531,264, filed Jul. 11, 2017.

FIELD OF THE INVENTION

This invention relates to polypeptide and protein controlled release pharmaceuticals that are made with hypercompression of biocompatible polymers.

BACKGROUND OF THE INVENTION

One of the many difficulties in the area of biotechnology is to achieve a technically viable methodology for long term sustained delivery of proteins. This is often due to the observation that proteins can be easily hydrolyzed and denatured. Encapsulated proteins in resorbable polymeric microparticles for prolonged release has been extensively studied. The problem of configuring a sustained release of large molecules, e.g. an easily injectable means of administration is due to the high porosity of microparticles, resulting in two key issues that have not been fully resolved: 1) exposing the protein payload to its surrounding water resulting in hydrolysis, 2) the resultant acidity from polymer degradation causing denaturation.

Hypercompressed polymers and copolymers containing pharmaceuticals are known. However, when a high molecular weight peptide or a protein is made into a controlled release pharmaceutical the stability of peptides and proteins to hypercompression has not previously been determined.

A significant factor affecting the interaction between carrier polymers and the reactive species of degraded peptides and proteins is their proximity to each other. Since hypercompression positions the reactive species in closer proximity to one another, the hypercompression actually can facilitate further degradation which results in a less stable product with a shorter shelf life.

Current pharmaceutical regulations exist in the United States and in Europe that limit the amount of substances in pharmaceuticals which are related to the active pharmaceutical ingredient to no more than 1.0 wt % or 5 µg TDI (total daily intake) whichever is lower. for a maximum daily dose of 1.0 mg. These requirements pose a challenge to formulators of controlled release products.

It is known that certain peptides and recombinant proteins have a short biological half-life and low oral bioavailability which has forced pharmaceutical manufacturers to only provide injectable formulations which complicate the therapy for which these materials are indicated. This is of special concern when protein based pharmaceuticals are administered to the eye which sometimes requires frequent the intraocular injection of a protein which is unpleasant for the patient and also carries with it the risk of infections and other complications.

Formulations have been prepared where proteins have been combined with ester terminated poly(DL lactic-co-glycolic acid)(PLGA capped) as a technique for providing controlled release formulations of proteins that can be administered by implantation or other techniques that avoid the need for direct injection. The controlled release of these formulations, that were not subjected to hypercompression, is modulated by the selection of different size particles of the protein loaded PLGA particles and different weight ratios of lactic acid to glycolic acid. The use of smaller particles (0.3 µm) of PLGA protein loaded particles has been found to result in a slower release (in PBS, pH 7.4) of protein than the use of larger particles (1.0-20 µm) having the same composition. The use of both the smaller and larger particles of the PLGA capped-protein loaded particles result in a controlled release product that has a pronounced burst effect when it is tested for controlled release properties. In an attempt to increase sustained delivery for a period of time, physical/chemical modifications of the protein or dispersed in medium, (hydrogels) is made.

It has been found that if a composition of a protein dispersed in a PLGA polymer is densified by hypercompression, the burst effect (which may cause toxicity, or excessive waste of drug that compromises duration) seen in PLGA polymer formulations is attenuated or avoided. The reduction of the burst effect also results in a formulation that will deliver a therapeutic effect for a longer period of time than an uncompressed product.

SUMMARY OF THE INVENTION

The invention provides a method for making a controlled release pharmaceutical product having a peptide or protein that is hypercompressed in combination with a lactide polymer, glycolide polymer or lactide-glycolide copolymer. The preferred polymer and copolymers are ester capped polymers and copolymers where the terminal acid group is reacted with an ester forming agent such as an alcohol, preferably a non-toxic aliphatic alcohol.

It is an object of this invention to provide an improved controlled release formulation of a lactide, glycolide or glycolactide polymer that is either an acid or an ester capped polymer or copolymer having a dispersed peptide or protein therapeutic agent having a reduced burst effect and a greater useful period of controlled release which can allow for extended intervals between the administration of peptide or protein based pharmaceuticals.

It is also an object of this invention to provide an improved controlled release formulation of a lactide, glycolide or glycolactide polymer that is an acid or ester capped polymer or copolymer having a dispersed peptide or protein therapeutic agent having a reduced burst effect and a reduced size relative to the amount of the drug loading in order to minimize any trauma caused by the introduction of the controlled release formulation into contact with a mucous membrane.

It is also an object of the invention to provide improved hypercompressed controlled release formulations of a peptide or protein that is stable to sterilization by electron beam radiation by hypercompressing the peptide or protein in combination with an ester capped lactide polymer, glycolide polymer or lactide-glycolide copolymer It is also an object of this invention to provide an improved control release formulation and method of administering an ophthalmic therapeutic agent which comprise a hypercompressed ophthalmic insert of a lactide, glycolide or lactide-glycolide polymer that is an acid or ester capped polymer or copolymer having a dispersed peptide or protein therapeutic agent having a weight average molecular weight from peptides with minimal molecular weight up to 250,000 or higher for complex macromolecules. Preferably the weight average molecular weight should be between 10,000 and 250,000.

BRIEF DESCRIPTION OF THE DRAWINGS

FIG. 1 is a graph of the release rates of the compressed formulations of bevacizumab from Example 1 (55 Kpsi) and Example 3 (135 Kpsi) with a control that had the same formulation except that the control was manually compacted at an estimated 1 Kpsi.

DETAILED DESCRIPTION OF THE INVENTION

Biodegradable polymers, such as poly(L-lactide) (PLLA) and poly(lactide-co-glycolide) (PLGA), are well known. They have been formulated as nanoparticles, microparticles, injectable depots, films, scaffolds, and as a bulk implant for drug delivery, due to their excellent toxicological profile and tunable biodegradability. Controlled drug delivery systems are important because they improve treatment and patient compliance, provide optimized drug concentration on site over prolonged periods, and reduce undesired side effects of the drug.

Drug delivery devices formulated from PLGA and PLA and other polymers have been studied for treating diseases of the eye as well as other areas, their hydrolytic degradation, drug release profiles, and mechanical integrity are optimized to suit various applications.

The present invention utilizes acid capped and/or ester capped lactide or glycolide or lactide-glycolide polymer or copolymer. These are known materials that are described in the chemical literature. The ester capped polymers are preferred and they may be prepared by esterification or transesterification of PLA or PGLA polymers or copolymers using an ester forming precursor such as an alcohol which will react with an acid terminal group of the PLA, PLGA or PG to form an ester capped polymer or copolymer. The ester groups include those having an alkyl group of 1-20 carbons atoms such as straight and branched chain alkyl groups although aromatic esters such as benzyl and phenyl may also be employed. A preferred ester capping agent is lauryl alcohol. The hypercompressed composition of the invention comprises an ester capped lactide, glycolide or lactide-glycolide polymer or copolymer that is combined with a peptide or protein therapeutic agent to form a controlled release dispensing unit. The therapeutic agents that may be mixed with the polymer or copolymer include: recombinant proteins including: Factor VIII, insulin, erythropoetin, vascular endothelial growth factor, fibroblast growth factor, lucocerebrosidase; antibodies for therapy including: abciximab, bevacizumab, pritumumab, ocrelizumab, infliximab and sarilumab; immunotoxins including: denileukin difititox, moxetumomab pasudotox, LMB-2, oportuzumab monatox, HuM195-gelonin, A-dmDT390 and bisFv(UCHT1); cytokines including granulocyte colony stimulating factor, interferon, tumor necrosis factor, interleukin and transformation growth factor-beta; ECM proteins including: elastin, collagen, fibronectin and pikachurin.

Prior to hypercompression, the acid or ester capped lactide or glycolide polymers or copolymers and an active pharmaceutical may be formed into microparticles known as microspheres or microcapsules which are typically in the size range of about 2 microns to about 50 microns, preferably from about 2 to about 25 microns and more preferably from about 5 to about 20 microns in diameter for the practice of the present invention. The term microsphere is used to describe a substantially homogeneous structure that is obtained by mixing an active drug with suitable solvents and polymers so that the finished product comprises a drug dispersed evenly in a polymer matrix which is shaped as a microsphere. Depending on the selected size range of the microparticles the term nanoparticle is used to describe structures sized from 1 to 1000 nanometers. A nanometer (nm) is one billionth of a meter or about the size of 10 hydrogen atoms. Currently, nanoparticle drug carriers mainly consist of solid biodegradable particles ranging from 50-500 nm in size. Generally a particle size should be selected so that the particles may be easily measured and transferred as necessary for the purpose of placing the particle in a suitable press for the application of hyper-compressive forces to form the compressed dosage form. The compressed particles are designated as the matrix which when placed in water or in contact with aqueous body fluids, such as the dermis, lung or intestine, will cause the compressed particles to disaggregate and form into the separate particles that were compressed to form the matrix.

An additional aspect of the invention is that once these microspheres are hyper-compressed, they result in an altered or distorted particle shape ranging in variation of degrees of elongation, circularity, and convexity or surface roughness that results from the application of hyper-compressive forces. The hypercompressed particles can be re-dispersed in a suitable aqueous vehicle for injection. Sterile normal saline or other isotonic solutions may be used for this purpose. Since the particle size of the hyper-compressed individual microspheres has been reduced, substantially more drug can be delivered using the same volume of microspheres.

Nanoparticles may be formed, for example, by sonicating a solution of polymer or copolymer in chloroform containing a 2% w/w solution of polyvinyl alcohol in the presence of the selected therapeutic agent for 10 minutes, using a ultrasonicator (Misonix XL-2020 at 50-55 W power output). Thereafter, the emulsion is stirred overnight at 4° C. to evaporate the chloroform and obtain nanoparticles of the polymer and the therapeutic agent.

Microcapsules are preferably used to form the compressed dosage forms of the invention. The term microcapsule is used to describe a dosage form, which is preferably nonspherical and has a polymer shell disposed around a core that contains the active drug and any added excipient which is in the size range set forth above. Generally microcapsules may be made by using one of the following techniques:

(1) phase separation methods including aqueous and organic phase separation processes, melt dispersion and spray drying;

(2) interfacial reactions including interfacial polymerization, in situ polymerization and chemical vapor depositions;

(3) physical methods, including fluidized bed spray coating; electrostatic coating and physical vapor deposition; and (4) solvent evaporation methods or using emulsions with an anti-solvent.

In general, the microparticles are comprised of from about 0.00001 to about 50 parts by weight of therapeutic agent and is further comprised of from about 50 to about 99.99999 parts by weight of polymer per 100 parts by weight of the total weight of therapeutic agent and polymer. The preferred ranges are from 1 to 50, 5 to 40, and 5 to 20 parts by weight of therapeutic agent, the balance comprised of polymer. If desired, from 1 to 5 wt % of a binder, such as polyvinyl pyrrolidone, may be homogeneously mixed with the microparticles prior to the compression step.

The amount of drug that is present in an implanted hypercompressed dosage form may vary but generally about 0.5-20 wt % or preferably about 3-5 wt % of the usual oral or intravenous dose of the drug may be employed but this may vary substantially depending on the solubility, the area of implantation, the patient and the condition to be treated. The total weight of the drug in the microcapsules may vary but will comprise about 1-5% of the total weight of the microspheres. Microspheres may be formed by a typical in-emulsion-solvent-evaporation technique as described herein.

In order to provide a biodegradable polymeric matrix for a controlled release dosage form which is suitable for placement in a position where a therapeutic agent may be released for treatment of a pathology, it is preferable to select the polymer from acid capped or ester capped poly(l-lactide), poly(dl-lactide), polyglycolide, poly(glycolide-co-lactide), poly(glycolide-co-dl-lactide), a block polymer of polyglycolide and trimethylene carbonate and a block polymer of poly-caprolactone and trimethylene carbonate or polyethylene oxide, or a mixture of any of the foregoing. The synthetic polymer may be a polylactide or a poly(lactide-co-glycolide) with any MW (weight average) or MW polydispersity, all ratios between lactic acid (LA) and glycolic acid (GA), and all degrees of crystallinity. Generally, the MW ranges from about 500 to about 10,000,000 Da, preferably from about 2,000 to about 1,000,000 Da, and more preferably from about 500 to about 5,000 Da. The p(LGA) with the ratio of LA:GA at about 75:25 to about 85:15 (mol:mol) and the MW from about 5,000 to about 500,000 may be used. The lactide/glycolide polymers are bulk-eroding polymers (not surface eroding polymers) and the polymer will hydrolyze when formed into a microparticle matrix as water enters the matrix and the polymer decreases in molecular weight. It is possible to shift the resorption curves to longer times by increasing the polymer molecular weight, using L-polymers and decreasing the surface area by increasing the size of the microparticles or the size of the dosage form. The lactide/glycolide copolymers are available with inherent viscosities as high as 6.5 dl/g and as low as 0.15 dl/g. The lower molecular weight copolymers are preferred for the present invention. It has been found that a mol ratio of 50:50 of glycolide to lactide results in the most rapid degradation and the corresponding release of drug. By increasing the ratio of lactide in the polymer backbone from about 50 mole % to 100% the rate of release can be reduced to provide an extended therapeutic effect from a single dosage unit.

A preferred encapsulating polymer is poly(glycolide-co-dl-lactide) capped with lauryl alcohol, which serves as the preferred controlled release delivery system for the dispensing device. The polymeric carrier serves as a sustained-release delivery system for the therapeutic agents. The polymers undergo biodegradation through a process whereby their ester bonds are hydrolyzed to form normal metabolic compounds, lactic acid and glycolic acid and allow for release of the therapeutic agent.

Copolymers consisting of various ratios of lactic and glycolic acids have been studied for differences in rates of degradation. It is known that the biodegradation rate depends on the ratio of lactic acid to glycolic acid in the copolymer, and the 50:50 copolymer degrades most rapidly. The selection of a biodegradable polymer system avoids the necessity of removing an exhausted non-biodegradable structure from the eye or other tissues, with the accompanying trauma.

After the microspheres are prepared, they are compressed at very high forces to form the dispensing device of the invention. The hyper-compression may be carried out in an apparatus that is capable or permits the application of from 50,000 to 350,000 psi (hereafter K is used in place of 1,000) pressure to microparticles or nanoparticles, or from 100 Kpsi to 300 Kpsi or 200 Kpsi to 300 Kpsi or 50 or 60 Kpsi to 160 or 170 Kpsi or especially 60 Kpsi to 170 Kpsi The term psi (pounds per square inch) is determined by taking the force in pounds that is applied to the particular dosage form and measuring or calculating the area of the top of the dosage form or die in square inches so that a conversion may be made to express the pressure applied to the dosage form in psi. The hyper-compressed dispensing device may be a perfect spheroid, but preferably a distorted spheroid such as a flat disc, rod, pellet with rounded or smooth edges that is small enough to be placed under the skin in a location such as bones and their joints, including the knuckles, toes, knees, hips and shoulders; glands, e.g. pituitary, thyroid, prostate, ovary or pancreas, or organs, e.g. liver, brain, heart, and kidney. More particularly, the dispensing device of the invention may be utilized to treat pathology by implanting the device at or near the site of the pathology, or in a way that will affect the pathology, such as any part that comprises the body of a human or animal or fish or other living species. Such parts may include the contents of a cell, any part of the head, neck, back, thorax, abdomen, perineum, upper or lower extremities. Any part of the osteology including but not limited to the vertebral column, the skull, the thorax, including the sternum or ribs, the facial bones, the bones of the upper extremity, such as the clavicle, scapula or humerus; the bones of the hand, such as the carpus; the bones of the lower extremity, such as the ilium or the femur; the foot, such as the tarsus; joints or ligaments; muscles and fasciae; the cardiovascular system, such as the heart, the arteries, the veins, or the capillaries or blood; the lymphatic system, such as the thoracic duct, thymus or spleen; the central or peripheral nervous system, the sensory organs, such as eye, ear, nose; the skin; the respiratory system, such as the lungs, the larynx, the trachea and bronchi; the digestive system, such as the esophagus, the stomach or the liver; the urogenital system, such as the urinary bladder, the prostate, or the ovary; the endocrine glands, such as the thyroid, the parathyroid or the adrenals.

Example 1

A 2 ml aliquot of a commercially available form of bevacizumab (Avastin®) solution containing 50 mg of bevacizumab (total weight of solids is ~186 mg including diluents/additives), is lyophilized. The lyophilized product in cake form is reduced to a powder with a spatula 1.25 g of an acid terminated PLGA (Purasorb PDLG7507 having an inherent viscosity of 0.56-0.84 dl/g. in 0.1 wt % in chloroform at 25° C. and a 75:25 wt. ratio of lactide to glycolide) is dissolved in methylene chloride to make a PLGA/MeCl$_2$ solution (a total of 5 ml). The powdered lyophilized Avastin® is added to the PLGA/MeCl$_2$ solution and gently dispersed in it. The tip of the generator, coupled to a homogenizer, is immersed in the lyophilized Avastin® powder and PLGA/MeCl$_2$ dispersion; the homogenizer is run at 7200 rpm for 60 seconds to form a s/o suspension. 20 ml of an aqueous 1% polyvinyl alcohol is then added to the Avastin® and PLGA/MeCl$_2$ solid-in-oil (s/o) suspension. The homogenizer is run for 60 seconds at 7200 rpm to form a solid-in-oil-in-water (s/o/w) emulsion, then, it is quickly poured into 300 ml of an aqueous 0.1% polyvinyl alcohol while stirring at 650 rpm on a magnetic stirrer, the stirring speed is reduced to 600 rpm after 30 minutes. After 3 hours, the suspension is centrifuged at 2500 rpm for 5 minutes and the microspheres formed are condensed and dispersed in 50 ml of double distilled water. The suspension is centrifuged at 2500 rpm to recover the microspheres, and this is repeated two more time. Finally, the microspheres are dispersed in 5 ml double distilled water, frozen at −70° C. and lyophilized.

These microspheres are hypercompressed at room temperature using a cylindrical shaped die having a diameter of 7.8 mm and a depth of 15.87 mm using a pressure of 55,000 psi to form a hypercompressed pellet. The hypercompressed pellet is then deposited in a 5 ml size Eppendorf tube containing 2 ml of phosphate buffered saline. Periodic withdrawals of an aliquot of 1.5 ml are taken from the tube (and replenished with an equal volume of phosphate buffered saline) and these aliquots are analyzed for the total bevacizumab present. A separate control is run on a minimally compacted microspheres. This data is used to prepare the curve in FIG. 1 that is labeled 55 Kpsi which illustrates the rate and the duration of the release of bevacizumab from acid capped PLGA.

Example 2

A 2 ml aliquot of a commercially available form of bevacizumab (Avastin®) solution containing 50 mg of bevacizumab (total weight of solids is ~186 mg including diluents/additives), is lyophilized. The lyophilized product in cake form is reduced to a powder with a spatula 1.1 g of an ester terminated PLGAe (Resomer RG755S having an inherent viscosity of 0.5-0.7 dl/g. in 0.1 wt % in chloroform at 25° C. and a 75:25 wt. ratio of lactide to glycolide) is dissolved in methylene chloride to make a PLGAe/MeCl$_2$ solution (a total of ~5 ml). The powdered lyophilized Avastin® is added to the PLGAe/MeCl$_2$ solution and gently dispersed in it. The tip of the generator, coupled to a homogenizer, is immersed in the lyophilized Avastin® powders and PLGAe/MeCl$_2$ dispersion; the homogenizer is run at 10000 rpm for 60 seconds to form a solid-in-oil (s/o) suspension. 20 ml of an aqueous 1% polyvinyl alcohol is then added to the Avastin® and PLGAe/MeCl$_2$ s/o suspension. The homogenizer is run for 60 seconds at 10000 rpm to form a solid-in-oil-in-water (s/o/w) emulsion, then, it is quickly poured into 300 ml of an aqueous 0.1% polyvinyl alcohol while stirring at 600 rpm on a magnetic stirrer. After 2½ hours, the suspension is centrifuged at 3000 rpm for 5 minutes and the microspheres formed are condensed and dispersed in 50 ml of double distilled water. The suspension is centrifuged at 3000 rpm to recover the microspheres, and this is repeated one or two more time. Finally, the microspheres are dispersed in double distilled water, frozen at −70° C. and lyophilized.

These microspheres are hypercompressed at room temperature using a cylindrical shaped die having a diameter of 7.8 mm and a depth of 15.875 using a pressure of 163000 psi to from a hypercompressed pellet. The hypercompressed pellet is then deposited in a 5 ml size Eppendorf tube containing 2 ml of phosphate buffered saline. Periodic withdrawals of an aliquot of 1.5 mL are taken from the tube (and replenished with an equal volume of phosphate buffered saline) and these aliquots are analyzed for the total bevacizumab present. A separate control is run on identically prepared microspheres that were manually compacted at room temperature using an estimated 1 Kpsi for the purpose of making a discrete and coherent control pellet.

Example 3

An additional sample was made using the procedure of Example 2 except that a pressure of 135,000 psi was used to form hypercompressed microspheres.

The invention claimed is:

1. A pharmaceutical dosage form which comprises an ester capped lactide, an ester capped glycolide, an ester capped lactide-glycolide polymer, an ester capped block polymer of polyglycolide, an ester capped trimethylene carbonate or an ester capped poly-caprolactone and is combined with a peptide or protein therapeutic agent in the form of microparticles which are compressed using a pressure of 50,000 to 350,000 psi.

2. A pharmaceutical dosage form as defined in claim 1 where the peptide or protein therapeutic agent is selected from the group consisting of recombinant proteins, antibodies for therapy, immunotoxins, cytokines and ECM proteins.

3. A pharmaceutical dosage form where the peptide or protein therapeutic agent as defined by claim 2 is bevacizumab.

4. A pharmaceutical dosage form as defined in claim 1 where the polymer is selected from the group consisting of ester capped poly(dl-lactide), polyglycolide, ester capped poly(glycolide-co-lactide), ester capped poly(glycolide-co-dl-lactide) or a mixture of any of the foregoing.

5. A pharmaceutical dosage form as defined in claim 1 where the microparticles have been compressed by the application of 50K psi to 170K psi.

6. A pharmaceutical dosage form as defined in claim 1 where the microparticles have been compressed by the application of 100 Kpsi to 300 Kpsi.

7. A pharmaceutical dosage form as defined in claim 1 where the microparticles have been compressed by the application of 60 Kpsi to 170 Kpsi.

8. A pharmaceutical dosage form as defined in claim 1 where the peptide or protein therapeutic agent is a recombinant protein.

* * * * *